United States Patent [19]

Heine et al.

[11] Patent Number: 5,371,094
[45] Date of Patent: Dec. 6, 1994

[54] AZAHETEROCYCLYLMETHYL-CHROMANS FOR TREATING AXIETY

[75] Inventors: Hans-Georg Heine, Krefeld; Rudolf Schohe-Loop, Wuppertal; Thomas Glaser, Overath; Jean M. V. De Vry, Roesrath; Wolfgang Dompert; Henning Sommermeyer, both of Cologne, all of Germany

[73] Assignee: Bayer Aktiengesellschaft, Leverkusen, Germany

[21] Appl. No.: 984,076

[22] Filed: Nov. 30, 1992

[30] Foreign Application Priority Data

Dec. 9, 1991 [DE] Germany .................. 4140540

[51] Int. Cl.$^5$ ................. A61K 31/445; C07D 405/14
[52] U.S. Cl. ........................... 514/323; 514/320; 514/322; 514/338; 514/339; 514/414; 546/156; 546/159; 546/200; 546/269; 546/271; 546/272; 548/454; 549/407
[58] Field of Search ........... 546/198, 15, 199, 197, 546/200, 270, 201, 271, 196, 272; 548/216, 221, 300.7, 305.1, 454; 514/320, 338, 321, 339, 322, 323, 373, 375, 387, 414

[56] References Cited

U.S. PATENT DOCUMENTS

| | | | |
|---|---|---|---|
| 3,759,927 | 9/1973 | Huebner | 546/20 |
| 3,826,835 | 7/1974 | Huebner | 546/20 |
| 3,845,060 | 10/1974 | Huebner | 546/20 |
| 4,153,612 | 5/1979 | McCall | 549/331 |
| 4,556,656 | 12/1985 | McCall | 546/199 |
| 4,711,960 | 12/1987 | McCall | 544/376 |
| 4,745,114 | 5/1988 | Elliott et al. | 514/233.5 |
| 4,957,928 | 9/1990 | Fröstl et al. | 514/318 |
| 5,112,855 | 5/1992 | Fröstl et al. | 514/456 |
| 5,137,901 | 8/1992 | Junge et al. | 514/373 |

FOREIGN PATENT DOCUMENTS 352613 1/1990 European Pat. Off. .

OTHER PUBLICATIONS

Glennon "Central cerotonine receptors are targets for Drug Research" J. Med Chem 30 1–12 (1987).
O'Brien "Receptor Binding in Drug Research" Marcel Dekker, Inc. pp. 418–419, 440–441 (1987).
Gotto et al "The role of receptors in biology and medicine" Raven Press, p. 191 (1986).
J. Traber et al., TIPS, vol. 8, 432 (1987).
M. Ennis, "Current Opinion in Investigational Drugs" (Apr. 1993).
Lozonczy et al., Pharmacology: 3rd generation of progress, H. Y. Melzer, p. 715, New York (1987).
Eur. J. Med. Chem. 22 (1987) 539–544.
Farmaco, Ed. Sci. 42 (11), 805–813 (1987).
J. Labelled, Comp., Pharm. 24, 909, 1987.
Aldrichimica Acta 18, 25, 1985.
Still et al, J. Org. Chem. 43, 2923, 1978.
Imafuku J. (1987), Brain Research 402; 331–338.
W. U. Dompert et al, Naunyn-Schmiedeberg's Arch. Pharmacol. (1985), 328, 467–470.

Primary Examiner—Celia Chang
Attorney, Agent, or Firm—Sprung Horn Kramer & Woods

[57] ABSTRACT

Azaheterocyclylmethyl-chromans are prepared by reaction of corresponding methylchromans with corresponding azaheterocyclic compounds, optionally with subsequent variation of the substituents. The azaheterocyclylmethyl-chromans can be used as active compounds in medicaments, in particular for the treatment of diseases of the central nervous system.

4 Claims, No Drawings

AZAHETEROCYCLYLMETHYL-CHROMANS FOR TREATING AXIETY

The invention relates to azaheterocyclylmethyl-chromans, processes for their preparation and their use in medicaments, in particular as agents for controlling diseases of the central nervous system.

It is already known that 2-benzofuranylmethyl derivatives have an activity on the central nervous system (compare German Patent Specification DE 2 165 276).

In addition, the compound 1-[(3,4-dihydro-2H-1-benzopyran-2-yl)methyl]piperidine in the form of its hydrochloride having an α-adrenergic-blocking effect is described in the publication Eur. J. Med. Chem. 22 (6), 539–544.

The invention relates to azaheterocyclylmethyl-chromans of the general formula (I),

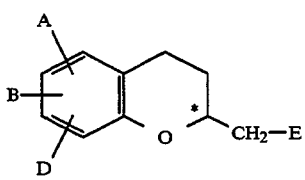

in which

A, B and D independently of one another represent hydrogen, halogen, cyano, azido, nitro, difluoromethyl, trifluoromethyl, difluoromethoxy, trifluoromethoxy, hydroxyl or carboxyl, or represent straight-chain or branched alkyl, alkenyl, acyl or alkoxycarbonyl having, in each case, up to 8 carbon atoms, or represent a group of the formula $-NR^1R^2$, $-NR^3-L-R^4$ or $-OR^5$, wherein $R^1$, $R^2$ and $R^3$ are identical or different and denote hydrogen, straight-chain or branched alkyl having up to 8 carbon atoms, phenyl or benzyl, L denotes the $-CO-$ or $-SO_2-$ group, $R^4$ denotes straight-chain or branched alkyl having up to 8 carbon atoms or benzyl, or denotes aryl having 6 to 10 carbon atoms, which is optionally substituted by halogen, hydroxyl, nitro, cyano, trifluoromethyl or trifluoromethoxy or by straight-chain or branched alkyl or alkoxy having up to 6 carbon atoms, and $R^5$ denotes straight-chain or branched alkyl or alkenyl having, in each case, up to 8 carbon atoms, which are optionally substituted by cycloalkyl having 3 to 6 carbon atoms or phenyl, or A has one of the abovementioned meanings and B and D together with the aromatic radical form a 5-membered to 7-membered saturated, partially unsaturated or aromatic carbocycle or heterocycle having up to 2 hetero atoms from the series S, N or O, the said cyclic radicals optionally being able to have up to 2 carbonyl functions in the ring and optionally being substituted, by up to 2 identical or different substituents, by straight-chain or branched alkyl, alkenyl or alkoxy having, in each case, up to 6 carbon atoms, hydroxyl, cycloalkyl having 3 to 6 carbon atoms, phenyl, halogen, cyano or nitro or, in a spiro-like manner, by a radical of the formula

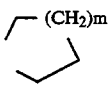

wherein m denotes a number 1 or 2, and

E represents a heterocyclic radical of the formula

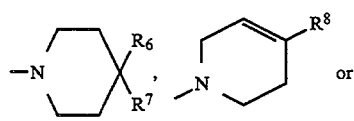

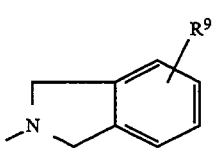

wherein $R^6$ denotes hydrogen, hydroxyl, halogen or phenyl, $R^7$ and $R^8$ independently of one another denote a straight-chain or branched alkyl having up to 8 carbon atoms, which must be substituted by a radical of the formula

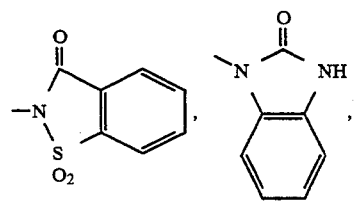

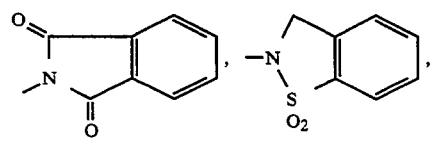

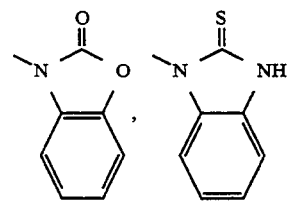

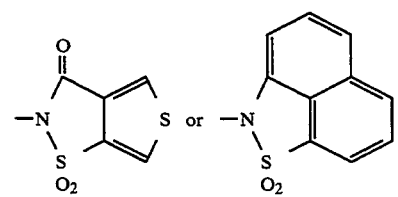

or denote a radical of the formula

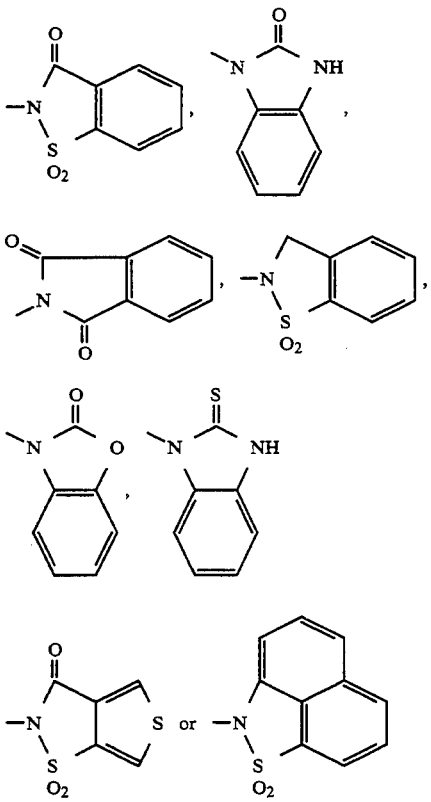

and

R⁹ denotes hydrogen, halogen, cyano, nitro, trifluoromethyl, trifluoromethoxy, hydroxyl or straight-chain or branched alkyl or alkoxy having, in each case, up to 6 carbon atoms, optionally in an isomeric form, and their salts.

Within the framework of the present invention, physiologically acceptable salts are preferred. Physiologically acceptable salts of the compounds according to the invention can be salts of the substances according to the invention with inorganic acids, carboxylic acids or sulphonic acids. Particularly preferred salts are, for example, salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Heterocycle in general represents a 5-membered to 7membered, preferably 5-membered to 6-membered, saturated or unsaturated ring, which can contain up to 2 oxygen, sulphur and/or nitrogen atoms as hetero atoms. 5-membered and 6-membered rings containing one oxygen, sulphur and/or up to 2 nitrogen atoms are preferred. The following are preferably mentioned: thienyl, furyl, pyrrolyl, pyrazolyl, pyranyl, pyridyl, pyrimidyl, pyrazinyl, pyridazinyl, thiazolyl, oxazolyl, imidazolyl, isoxazolyl, pyrrolidinyl, piperidinyl, piperazinyl, tetrazolyl, morpholinyl or dioxanyl.

Within the framework of the present invention the compounds according to the invention can be present in various stereoisomeric forms. The compounds according to the invention exist in stereoisomeric forms which are either related to one another as image and mirror image (enantiomers) or are not related to one another as image and mirror image (diastereoisomers). The invention relates both to the antipodes and the racemic forms and to the mixtures of diastereoisomers. The racemic forms can be separated in the same way as the diastereoisomers in a known manner into the single stereoisomer constituents [compare E.L. Eliel, Stereochemistry of Carbon Compounds, McGraw Hill, 1962].

Preferred compounds of the general formula (I) are those in which

A, B and D independently of one another represent hydrogen, fluorine, chlorine, bromine, cyano, trifluoromethyl, difluoromethoxy, trifluoromethoxy or hydroxyl, or represent straight-chain or branched alkyl, alkenyl, acyl or alkoxycarbonyl having, in each case, up to 6 carbon atoms, or represent a group of the formula —NR¹R²—NR³—L—R⁴ or —OR⁵, wherein R¹, R² and R³ are identical or different and denote hydrogen or straight-chain or branched alkyl having up to 6 carbon atoms, L denotes the —CO— or —SO²— group, R⁴ denotes straight-chain or branched alkyl having up to 6 carbon atoms or benzyl, or denotes phenyl which is optionally substituted by fluorine, chlorine, bromine, trifluoromethyl, trifluoromethoxy or hydroxyl or by straight-chain or branched alkyl or alkoxy having, in each case, up to 4 carbon atoms, and R⁵ denotes straight-chain or branched alkyl or alkenyl having up to 6 carbon atoms, which are optionally substituted by cyclopropyl, cyclopentyl, cyclohexyl or phenyl, or A has one of the abovementioned meanings and B and D together form a radical of the formula

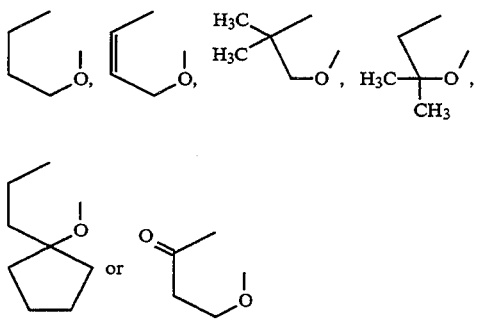

and

E represents a heterocyclic radical of the formula

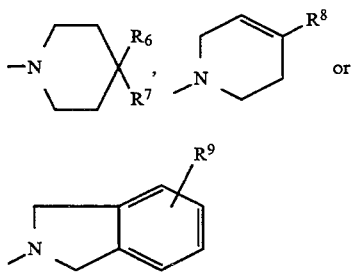

wherein

R[6] denotes hydrogen, hydroxyl, fluorine, chlorine, bromine or phenyl, R[7] and R[8] independently of one another denote straight-chain or branched alkyl having up to 6 carbon atoms, which must be substituted by a radical of the formula

[chemical structures]

or denote a radical of the formula

[chemical structures]

and

R[9] denotes hydrogen, fluorine, chlorine, bromine, trifluoromethyl, hydroxyl or straight-chain or branched alkyl or alkoxy having, in each case, up to 4 carbon atoms, optionally in an isomeric form,
and their salts.

Particularly preferred compounds of the general formula (I) are those
in which
A, B and D independently of one another represent hydrogen, fluorine, chlorine, bromine, cyano, trifluoromethyl, trifluoromethoxy or hydroxyl, or represent straight-chain or branched alkyl or alkenyl having, in each case, up to 4 carbon atoms, or represent a group of the formula —NR¹R² or —OR⁵,
wherein
R¹ and R² are identical or different and denote hydrogen or straight-chain or branched alkyl having up to 4 carbon atoms, and
R⁵ denotes straight-chain or branched alkyl or alkenyl having up to 4 carbon atoms, which are optionally substituted by cyclopropyl or phenyl,
or
A has one of the abovementioned meanings
and
B and D together form a radical of the formula

[chemical structures]

E represents a heterocyclic radical of the formula

[chemical structures]

wherein
R[6] denotes hydrogen, hydroxyl, fluorine or chlorine,
R[7] and R[8] independently of one another denote straight-chain or branched alkyl having up to 4 carbon atoms, which must be substituted by a radical of the formula

[chemical structures]

or denote a radical of the formula

[chemical structures]

and

R⁹ denotes hydrogen, fluorine, chlorine, trifluoromethyl, hydroxyl, methyl, ethyl, methoxy or ethoxy, optionally in an isomeric form, and their salts.

In addition, processes for the preparation of the compounds according to the invention of the general formula (I) have been found, characterised in that

[A] Compounds of the general formula (II)

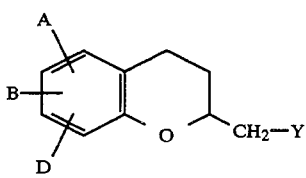
(II)

in which

A, B and D have the abovementioned meaning and

Y represents hydroxyl or represents a typical leaving group, such as, for example, tosylate, chloride or mesylate, preferably tosylate, are reacted directly with compounds of the general formula (III)

  H—E  (III), in which

E has the abovementioned meaning, in inert solvents, in the presence of a base and optionally of an auxiliary (catalyst, starter), or

[B] in the case where R⁷ represents a radical of the formula —T—R¹⁰, wherein

T denotes straight-chain or branched alkyl having up to 8 carbon atoms and

R¹⁰ represents one of the heterocyclic radicals mentioned above under R⁷, compounds of the general formula (IV),

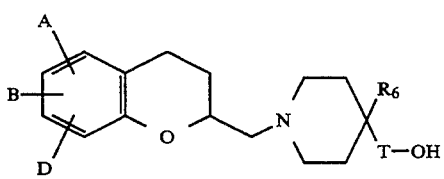
(IV)

in which

A, B, D, R⁶ and T have the abovementioned meaning, are reacted with compounds of the general formula (V)

  H—R¹⁰  (V)

in which

R¹⁰ has the abovementioned meaning, in inert solvents in a Mitsunobu reaction, and, optionally, reductions are carried out by conventional methods, and in the case of the enantiomers, either the compounds of the general formula (III) are reacted with compounds of the general formula (II) which are in the form of a single enantiomer, or the corresponding racemates of the compounds of the general formula (I) are separated by the known methods for racemate separation described above, for example by separation via salts with acids in the form of a single enantiomer, and, optionally, the substituents A, B and D are converted to derivatives, likewise by known methods.

The processes according to the invention can be illustrated by way of example by the following equation:

[A]

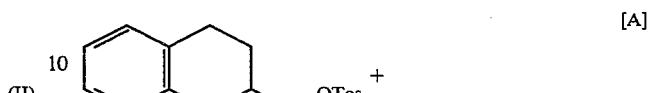

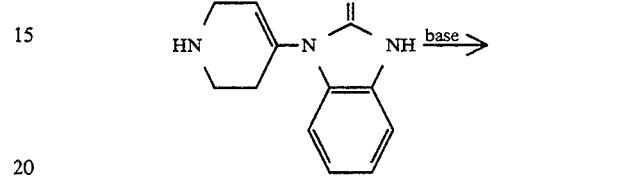

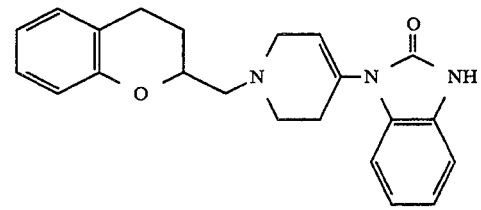

[B]

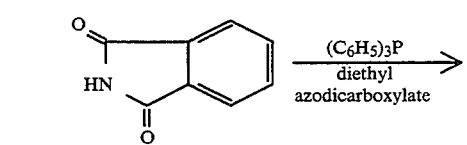

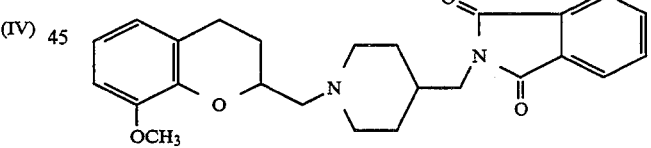

Suitable solvents for the reaction with the amines of the general formula (III) are the conventional solvents which do not change under the reaction conditions. These preferably include alcohols, such as methanol, ethanol, propanol or isopropanol, or ethers, such as diethyl ether, dioxane, tetrahydrofuran, glycol dimethyl ether or butyl methyl ether, or ketones, such as acetone or butanone, or amides, such as dimethylformamide or hexamethylphosphoric acid triamide, or dimethylsulphoxide, acetonitrile, ethyl acetate or halogenated hydrocarbons, such as methylene chloride, chloroform or carbon tetrachloride, or pyridine, picoline or N-methylpiperidine. Mixtures of the said solvents can also be used. Methanol, ethanol, propanol, isopropanol or dimethylformamide are preferred.

Suitable bases are the conventional inorganic or organic bases. These preferably include alkali metal hydroxides, such as sodium hydroxide or potassium hydroxide, or alkali metal carbonates, such as sodium carbonate or potassium carbonate, or alkali metal alcoholates, such as, for example, sodium methanolate, potassium methanolate, sodium ethanolate or potassium ethanolate, or organic amines, such as triethylamine, picoline, pyridines or N-methylpiperidine, or amides, such as sodium amide or lithium diisopropylamide. Sodium carbonate, potassium carbonate and pyridine are preferred.

The bases are used in an amount of 0.5 mol to 10 mols, preferably of 0.3 mol to 3 mols, based on 1 mol of the compounds of the general formula (II). In the case of pyridine, the base can also be used as solvent.

The reaction is generally carried out in a temperature range of 0° C. to 150° C., preferably of +20° C. to +110° C.

The reaction can be carried out under normal, elevated or reduced pressure (for example 0.5 to 5 bar). In general the reaction is carried out under normal pressure.

The reductions can in general be carried out by hydrogen in water or in inert organic solvents, such as alcohols, ethers or halogenated hydrocarbons, or mixtures thereof, using catalysts such as Raney nickel, palladium, palladium-on-animal charcoal or platinum, or using hydrides or boranes in inert solvents, if appropriate in the presence of a catalyst.

The reaction is preferably carried out using hydrides, such as complex borohydrides or aluminium hydrides. In this context, sodium borohydride, lithium aluminium hydride or sodium cyanoborohydride are particularly preferably employed.

Suitable solvents in this context are all inert organic solvents which do not change under the reaction conditions. These preferably include alcohols, such as methanol, ethanol, propanol or isopropanol, or ethers, such as diethyl ether, dioxane, tetrahydrofuran, glycol dimethyl ether or diethylene glycol dimethyl ether, or amides, such as hexamethylphosphoric acid triamide or dimethylformamide, or acetic acid. It is also possible to use mixtures of the said solvents.

The catalysts used in the reduction with sodium cyanoborohydride are in general protic acids. These preferably include inorganic acids, such as, for example, hydrochloric acid or sulphuric acid, or organic carboxylic acids having 1-6 C atoms, optionally substituted by fluorine, chlorine and/or bromine, such as, for example, acetic acid, trifluoroacetic acid, trichloroacetic acid or propionic acid, or sulphonic acids containing $C_1$–$C_4$-alkyl radicals or aryl radicals, such as, for example, methanesulphonic acid, ethanesulphonic acid, benzenesulphonic acid or toluenesulphonic acid.

The Mitsunobu reaction generally proceeds in one of the non-protic solvents indicated above, preferably tetrahydrofuran, in the presence of phosphanes, preferably triphenylphosphane, and ester derivatives of azodicarboxylic acid, preferably diethyl azodicarboxylate, in a temperature range of 0° C. to +50° C., preferably at room temperature and normal pressure [in this context compare O. Mitsunobu, Synthesis 1981,1].

The compounds of the general formula (II) are known per se or can be prepared by conventional methods [compare German Patent Specification 3 620 408 A, U.S. Pat. No. 4 957 928, Farmaco, Ed. Sci. 42 (11), 805-813], it being possible to obtain compounds in the form of a single enantiomer by using the corresponding chroman-2-carboxylic acids in the form of a single enantiomer and their derivatives for the preparation [in this context compare J. Labelled Comp. Pharm. 24, 909, 1987].

The amines of the general formula (III) are known, can be prepared by conventional methods or are available commercially [compare MSD Book 2, 2846 D; Beilstein 21 (2) 8].

The majority of the compounds of the general formula (IV) are novel and can then be prepared, for example, by reducing in inert solvents, the corresponding compounds of the general formula (VI)

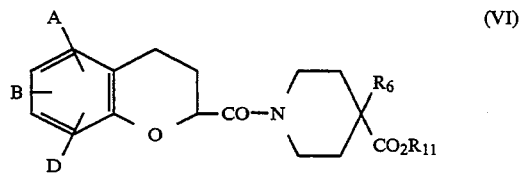

in which
A, B, D and $R^6$ have the abovementioned meaning
and
$R^{11}$ represents $C_1$–$C_4$-alkyl.

The reduction of the acid amides and imides is effected using hydrides in inert solvents or using boranes, diboranes or their complex compounds.

The reactions are preferably carried out using hydrides, such as complex borohydrides or aluminiumhydrides, as well as boranes. In this context, sodium borohydride, lithium aluminium hydride, sodium bis-(2-methoxyethoxy)aluminium hydride or borane-tetrahydrofuran are particularly preferably employed.

The reaction can be carried out under normal, elevated or reduced pressure (for example 0.5 to 5 bar). In general the reaction is carried out under normal pressure.

The reduction is in general effected in a temperature range of −50° C. up to the boiling point of the particular solvent, preferably of −20° C. to +90° C.

The compounds of the general formula (VI) are known in some cases or are novel and can be prepared, for example, by reacting the corresponding activated chroman-2-carboxylic acid derivatives with piperidine-4-carboxylic acid esters in inert solvents, preferably pyridine, in the presence of one of the abovementioned bases, preferably pyridine.

The compounds according to the invention can be used as active compounds in medicaments. The substances according to the invention have a particularly high affinity for cerebral 5-hydroxy-tryptamine receptors of the 5-HT$_1$ type. They also have high affinity for dopamine receptors of the D$_2$ type.

The substances according to the invention surprisingly show an advantageous effect on the central nervous system and can be used for the therapeutic treatment of humans and animals.

The compounds described in the present invention are thus active compounds for controlling diseases which are characterised by disorders of the serotoninergic and dopaminergic system, in particular in the case of the involvement of receptors which have high affinity for 5-hydroxytryptamine (5-HT$_1$ type) and/or for dopamine (D$_2$ type). They are therefore suitable for the treatment of diseases of the central nervous system, such as anxiety, stress and depressive states, sexual dysfunctions related to the central nervous system and sleep disorders, and for regulating pathological disorders of food, coffee, tea, tobacco, alcohol and addictive drug intake.

They are also suitable for the elimination of cognitive deficits, for the improvement of learning and memory performance and for the treatment of Alzheimer's disease. They are also suitable for controlling psychoses (for example schizophrenia, mania). Compared with known neuroleptic agents, they have a lower potential for side effects.

Furthermore, these active compounds are also suitable for modulation of the cardiovascular system. They also intervene in regulation of the cerebral circulation and are thus effective agents for controlling migraine.

They are also suitable for the prophylaxis and control of the consequences of cerebral infarct events (apoplexia cerebri), such as stroke and cerebral ischaemias. Moreover, the compounds can be used for the treatment of acute craniocerebral trauma. The compounds according to the invention can also be used to control states of pain.

Affinity for the 5-HT$_1$ receptor

The high affinity of the compounds according to the invention for 5-hydroxytryptamine receptors of subtype 1 is shown in Table 1 by way of example. The values shown are data which have been determined from receptor-binding studies using calf hippocampus membrane preparations. To this end, aH-serotonin was used as radioactively labelled ligand.

TABLE [A]

| Compound of Example | K$_i$ (nmol/l) |
|---|---|
| 2 | 3 |
| 4 | 2 |

Affinity for the 5-HT$_{1A}$ receptor

[W.U. Dompert et al., Naunyn-Schmiedeberg's Arch. Pharmacol. (1985), 328, 467–470].

In this test the binding of $^3$H-ipsapiron to 5-HT$_{1A}$ receptors in calf hippocampus membranes is measured. It was found that the compounds according to the invention compete for the binding with the radioligand and inhibit them.

TABLE [B]

| Compound of Example | K$_i$ (nmol/l) |
|---|---|
| 5 | 1.5 |
| 6 | 1.4 |

Dopamine D$_2$ receptor test

This test is carried out in accordance with the following literature reference: Imafuku J. (1987), Brain Research 402; 331–338.

In this test the binding of the selective D$_2$ receptor antagonist $^3$H-sulpiride to membranes from the striatum of rats is measured. Compounds which bind to dopamine D$_2$ receptors inhibit the binding of $^3$H-sulpiride in a concentration-dependent manner. IC$_{50}$ values are determined from the displacement curves and the inhibition constants K$_i$ calculated from these values.

TABLE [C]

| Compound of Example | K$_i$ (nmol/l) |
|---|---|
| 2 | 1.8 |
| 3 | 0.4 |
| 6 | 2.3 |

The present invention also includes pharmaceutical preparations which contain, in addition to inert, non-toxic, pharmaceutically suitable auxiliaries and excipients, one or more compounds of the general formula (I), or which consist of one or more active compounds of the formula (I), as well as processes for the production of these preparations.

The active compounds of the formula (I) should be present in these preparations in a concentration of 0.1 to 99.5% by weight and preferably of 0.5 to 95% by weight of the total mixture.

In addition to the active compounds of the formula (I), the pharmaceutical preparations can also contain other pharmaceutical active compounds.

The abovementioned pharmaceutical preparations can be prepared in a conventional manner by known methods, for example using the auxiliary or auxiliaries or excipient(s).

In general, it has proved advantageous to administer the active compound or active compounds of the formula (I) in total amounts of about 0.01 to about 100 mg/kg, preferably in total amounts of about 1 mg/kg to 50 mg/kg of body weight per 24 hours, optionally in the form of several single doses, in order to achieve the desired results.

However, it can, where appropriate, be advantageous to deviate from the said amounts and specifically to do so as a function of the nature and the body weight of the object to be treated, of the individual behaviour towards the medicament, the nature and severity of the disease, the type of preparation and application and the time or interval at which administration takes place.

Unless indicated otherwise, the R$_f$ values mentioned in each case were determined by thin layer chromatography on silica gel (aluminiumfoil, silica gel 60 F 254, E. Merck). The substance spots were visualised by observing under UV light and/or by spraying with 1% strength potassium permanganate solution.

Flash chromatography was carried out on silica gel 60, 0.040–0.064 mm, E. Merck (see Still et al., J. Org. Chem. 43, 2923, 1978: for simpler separation problems see Aldrichimica Acta 18, 25, 1985). Elution using solvent gradients denotes: Starting with the pure, nonpolar solvent mixture component, the polar eluent component is admixed in an increasing proportion until the desired product is eluted (TLC control).

For all products, the solvent was distilled off under, finally, about 0.1 mmHg. Salts were stored under this pressure overnight over potassium hydroxide and/or phosphorus pentoxide.

STARTING COMPOUNDS

Example I

8-Methoxy-chroman-2-carboxylic acid (4-ethoxycarbonyl)piperidide

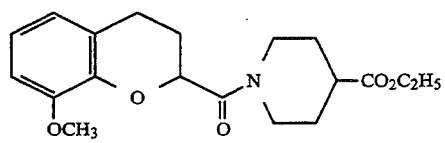

9.0 g (40 mmol) of 8-methoxy-chroman-2-carboxylic acid chloride are added in several portions to 6.3 g of ethyl piperidine-4-carboxylate (40 mmol) and 0.1 g of 4-dimethylaminopyridine in 20 ml of anhydrous pyridine. After 40 hours at room temperature, the mixture is poured onto ice. The solid which precipitates after 30 minutes is washed with water and dried in a desiccator.

Yield: 6.2 g (45 %)

This material is further used without further purification.

Example II

2-Hydroxymethyl-8-methoxy-chroman

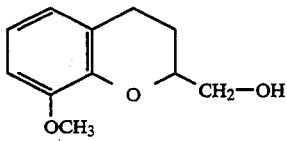

59.0 g (0.25 mol) of ethyl 8-methoxy-chroman-2-carboxylate in 525 ml of anhydrous tetrahydrofuran are added dropwise in the course of 1 h, with stirring, at 20° C. to a suspension of 9.5 g (0.25 mol) of lithium aluminium hydride in 525 ml of anhydrous diethyl ether. The batch is stirred overnight and 9.5 ml of water, 9.5 ml of 15% strength sodium hydroxide solution and 28.4 ml of water are then successively added dropwise, with cooling. The organic phase is decanted off and evaporated. The residue is recrystallised twice from dichloromethane/petroleum ether.

Yield: 38.0 g (87%)

Melting point: 57°-58° C.

Example III (2R)-2-Hydroxymethyl-chroman

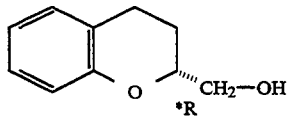

164 ml of a 1 M solution of borane in tetrahydrofuran is added dropwise in the course of 30 minutes to a solution of 22.1 g (0.124 mol ) of (2R) -chroman-2-carboxylic acid (ee=98.3%) in 210 ml of anhydrous tetrahydrofuran under argon, at an internal temperature of 0° C. The cooling is removed and the batch is stirred for a further 4 h. The internal temperature rises during this period to 34° C. 46 ml of a 1/1 mixture of tetrahydrofuran and water are then added dropwise, with ice cooling. After adding 40.7 g of anhydrous potassium carbonate and stirring vigorously, the tetrahydrofuran solution is decanted and concentrated under a water pump vacuum. Short-path distillation yields 18.8 g of colourless 2R-hydroxymethylchroman having a boiling point of 77°-78° C./0.15 mbar. ee>99%.

Example IV (2S)-2-Hydroxymethyl-chroman

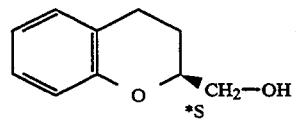

The title compound is prepared from (2S)-2-chroman-2-carboxylic acid analogously to the method of Example II. ee>99%

Boiling point: 79°-81° C./0.15 mbar

Example V (2R)-2-Tosyloxymethyl-chroman

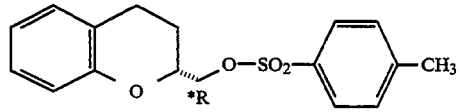

15.63 g (0.082 mol) of 4-toluenesulphonyl chloride are added in portions to 12.8 g (0.078 mol) of (2R)-2-hydroxymethylchroman (Example II) in 50 ml of anhydrous pyridine, with stirring and ice cooling. After leaving to stand overnight, the batch is introduced into ice-water and extracted with diethyl ether. The ether phase is washed twice with 5% strength ice-cold hydrochloric acid and then with saturated sodium chloride solution, dried over anhydrous sodium sulphate and evaporated under a water pump vacuum. 22.4 g of 2R-2-hydroxymethylchroman 4-toluenesulphonate in the form of a single compound are obtained.

$R_f$=0.6 (toluene/ethyl acetate 3:1) oil

Melting point: 62°-65° C. (petroleum ether/dichloromethane)

$[\alpha]_D$ =51.1° (c=1, chloroform)

Example VI (2S)-2-Tosyloxymethyl-chroman

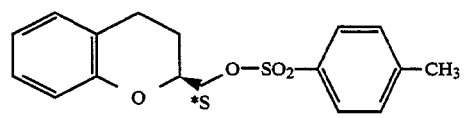

The title compound from Example III is prepared analogously to the method of Example IV.

$R_f$=0.6 ( toluene/ethyl acetate 3:1) oil

Example VII

8 -Methoxy-2 -tosyloxymethyl-chroman

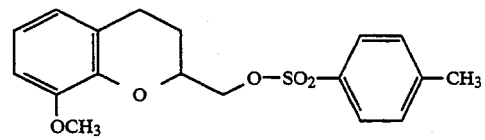

Melting point: 115°-117° C. (from dichloromethane)

Example VIII

2-Phthalimidomethyl-8-methoxy-chroman

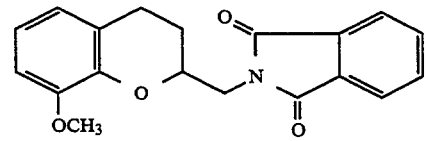

By reacting the compound from Example II with phthalimide in the presence of equimolar amounts of triphenylphosphane and diethyl azodicarboxylate in tetrahydrofuran, the desired product is obtained in 80%

Example IX

2-[(4-Hydroxymethyl)-piperidin-1-yl]methyl-8-methoxychroman hydrochloride

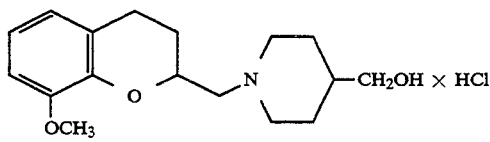

31 ml of a 3.4 M solution of sodium bis-(2-methoxyethoxy)-dihydroaluminate in toluene are added to 5.2 g (15 mmol) of the compound from Example I in 31 ml of toluene and the mixture is stirred for 18 h at 50° C. under argon. After dilution with toluene, the reaction mixture is hydrolysed with 10 ml of 1:1 mixture of tetrahydrofuran and water. Filtration and flash chromatography of the filtrate (silica gel, toluene/i-propanol - gradient 100:0 to 50:50) yields the product in the form of the free base; 2.8 g (64%) in the form of a syrup. By treatment with ethereal hydrochloric acid, the hydrochloride is obtained, which is recrystallised from acetonitrile.

Melting point: 107°–112° C. (after recrystallisation from acetonitrile)

IR (KBr): 3510, 3301(b), 2945, 2548(b), 1630(w), 1583(w), 1481

The compounds listed in Table I are prepared analogously to the methods of Examples I and IX:

TABLE I

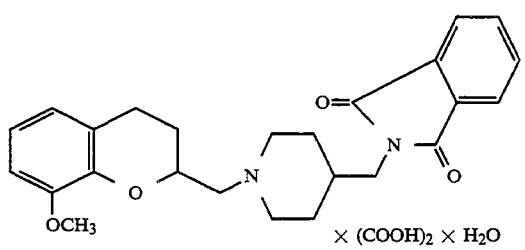

| Ex. No. | X | Y | m.p. °C. | Preparation analogous to Example |
|---|---|---|---|---|
| X | —CO | —CO$_2$C$_2$H$_5$ | 64–66 (from petroleum ether/ether) | I |
| XI | —CH$_2$ | —CH$_2$OH | oil | IX |

PREPARATION EXAMPLES

Example 1

2-(1H-2,3-dihydro-2-indol-2-yl)methyl-8-methoxychroman hydrochloride

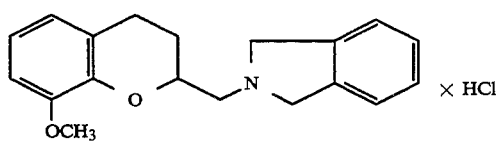

7.3 g (23 mmol) of the compound from Example VIII in 50 ml of tetrahydrofuran are added dropwise to 2.5 g (68 mmol) of lithium aluminium hydride in 80 ml of diethyl ether. The mixture is refluxed for 5 hours and then left to stand for 15 hours at room temperature. 10 ml of water in 30 ml of tetrahydrofuran, followed by 5 ml of 45% sodium hydroxide solution are added dropwise. After filtering through kieselguhr and rinsing the solid with toluene/ethyl acetate 1/1, a filtrate is obtained which is concentrated in a rotary evaporator. Flash chromatography (silica gel, toluene/ethyl acetate gradient 100:0 to 75:25) yields 6.2 g (93%) of the desired product in the form of the free base (syrup). The hydrochloride is obtained from this base by treatment with ethereal hydrochloric acid.

Melting point: 256°–258° C. (after recrystallisation from 2-propanol)

R$_f$=0.35 (silica gel, toluene/ethyl acetate 1:1)
MS (EI): 295, 132 (100%), 105, 36

EXAMPLE 2

2-[4-(Isoindol-1,3-dion-2-yl)methyl-piperidin-1-yl)methyl-8-methoxychroman oxalate hydrate

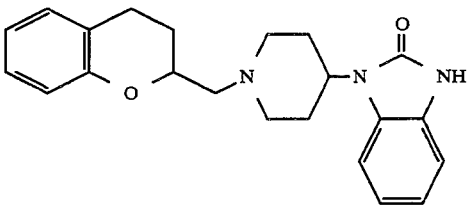

4.1 g (14 mmol) of the compound from Example IX, 4.1 g (15 mmol) of triphenylphosphine and 2.3 g (15 mmol) of phthalimide are dissolved in 6 ml of dry tetrahydrofuran. 2.7 g of diethyl azodicarboxylate in 10 ml of tetrahydrofuran are added dropwise to this solution at room temperature. After 10 days at room temperature, the reaction mixture is concentrated and the residue digested with cyclohexane. Insoluble matter is filtered off and the filtrate is concentrated in a rotary evaporator. Chromatography (silica gel, toluene/ethyl acetate 100:0 to 50:50) and rechromatography (silica gel, dichloromethane/ 2-propanol 50:1 to 10:1) yields the desired product in the form of an oil (1.15 g). The hydrochloride (1.15 g, 16%) is precipitated from this oil by treatment with ethereal hydrochloric acid. For further purification, the base is liberated from the hydrochloride using sodium bicarbonate solution. The oxalate, which is accessible by adding oxalic acid dihydrate in ethanolic solution, is recrystallised from acetonitrile. Further recrystallisation from 2-propanol yields 0.30 g of analytically pure title compound after cooling to −36° C.

Melting point: >70° C. (decomposition)
R$_f$=0.3 (silica gel, dichloromethane/2-propanol 20:1)

EXAMPLE 3

1-(Chroman-2-yl-methyl)-4-(2-oxo-1-benzimidazolyl)piperidine

The mixture of 8.8 g (27.7 mmol) of (chroman-2R,S-ylmethyl) 4-toluenesulphonate, 2.1 g (20 mmol) of anhydrous sodium carbonate and 6.5 g (30 mmol) of 4-(2-oxo-1-benzimidazolinyl)-piperidine in 70 ml of anhydrous dimethylformamide is stirred for 6 h at 110° C. and then poured onto ice (250 g). After extracting with ethyl acetate, washing the organic extracts with water, drying over anhydrous sodium sulphate and evaporating the organic phase under a water pump vacuum, 9.8 g of crystalline crude product which is virtually a single compound are obtained, which product is twice recrystallised from dichloromethane/petroleum ether for analysis. Melting point: 107°–109° C. (cap.)

The examples listed in Tables 1 and 2 were prepared analogously to the method of Example 3.

TABLE 1

| Ex. No. | A | B | E | m.p. °C. |
|---|---|---|---|---|
| 4 | —OCH$_3$ | H |  | 196–197 (free base) |
| 5 | H | H |  | 138–140 (free base) |
| 6 | —OCH$_3$ | H |  | 167–169 (free base) |

TABLE 2

| Ex. No. | Z | m.p. °C. |
|---|---|---|
| 7 |  | 167–168 (free base) $\alpha_D = -51.2$ (c = 0.6, THF) |

TABLE 2-continued

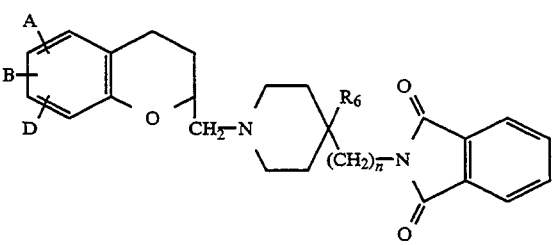

| Ex. No. | Z | m.p. °C. |
|---|---|---|
| 8 |  | 167–168 $\alpha_D = +53.9$ (c = 0.6, THF) |

We claim:

1. An azaheterocyclylmethyl-chroman of the formula:

in which
A, B and D independently of one another represent hydrogen, halogen, cyano, azido, nitro, difluoromethyl, trifluoromethyl, difluoromethoxy, trifluoromethoxy, hydroxyl or carboxyl; or
represent straight-chain or branched alkyl, alkenyl, alkanoyl or alkoxycarbonyl having, in each case, up to 8 carbon atoms; or
represent a group of the formula —NR$^1$R$^2$—NR$^3$—L—R$^4$ or —OR$^5$;
wherein
R$^1$, R$^2$ and R$^3$ are identical or different and represent hydrogen, straight-chain or branched alkyl having up to 8 carbon atoms, phenyl or benzyl;
L represents —CO— or —SO$_2$;
R$^4$ represents straight-chain or branched alkyl having up to 8 carbon atoms or benzyl, or denotes hydrocarbyl aryl having 6–10 carbon atoms, which is optionally substituted by halogen, hydroxyl, nitro, cyano, trifluoromethyl or trifluoromethoxy or by straight-chain or branched alkyl or alkoxy having up to 6 carbon atoms;
R$^5$ represents straight-chain or branched alkyl or alkenyl having, in each case, up to 8 carbon atoms, which are optionally substituted by cycloalkyl having 3 to 6 carbon atoms or phenyl;
R$^6$ denotes hydrogen, hydroxyl, halogen or phenyl; and
n represents an integer 1–8;
optionally in an isomeric form,
or a salt thereof.

2. A compound according to claim 1 wherein such compound is 2-[4-(isoindol-1,3-dion-2-yl)methyl-piperidin-1-yl]-methyl-8-methoxy-chroman of the formula

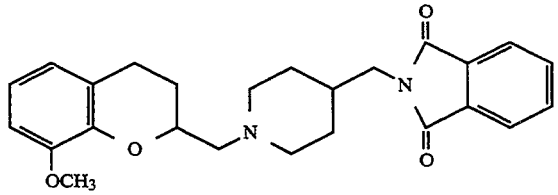

or a salt thereof.

3. A composition for treating anxiety said composition comprising an amount effective to control said disease of an azaheterocyclylmethyl-chroman according to claim 1 in admixture with a pharmaceutically acceptable excipient.

4. A method of treating anxiety, said method comprising administering to a patient in need thereof an amount effective to control said disease of an azaheterocyclylmethyl-chroman according to claim 1.

* * * * *

UNITED STATES PATENT AND TRADEMARK OFFICE
CERTIFICATE OF CORRECTION

PATENT NO. : 5,371,094

DATED : December 6, 1994

INVENTOR(S) : Heine, et al.

It is certified that error appears in the above-identified patent and that said Letters Patent is hereby corrected as shown below:

On the Title page, and in Col. 1, line 2, item [54] Invention: delete "AXIETY" and substitute --ANXIETY--.

Signed and Sealed this

Second Day of May, 1995

Attest:

BRUCE LEHMAN

*Attesting Officer*      *Commissioner of Patents and Trademarks*